(12) United States Patent
Raupach et al.

(10) Patent No.: US 10,060,870 B2
(45) Date of Patent: Aug. 28, 2018

(54) METHOD AND APPARATUS FOR MONITORING AN UNDERGROUND OBJECT

(71) Applicant: RHEINISCH-WESTFÄLISCHE TECHNISCHE HOCHSCHULE AACHEN, Aachen (DE)

(72) Inventors: Michael Raupach, Aachen (DE); Kenji Reichling, Berlin (DE); Christian Helm, Aachen (DE)

(73) Assignee: RHEINISCH-WESTFAELISCHE TECHNISCHE HOCHSCHULE AACHEN, Aachen (DE)

( * ) Notice: Subject to any disclaimer, the term of this patent is extended or adjusted under 35 U.S.C. 154(b) by 43 days.

(21) Appl. No.: 15/029,998

(22) PCT Filed: Nov. 13, 2014

(86) PCT No.: PCT/EP2014/003040
§ 371 (c)(1),
(2) Date: Apr. 28, 2016

(87) PCT Pub. No.: WO2015/070982
PCT Pub. Date: May 21, 2015

(65) Prior Publication Data
US 2016/0313271 A1    Oct. 27, 2016

(30) Foreign Application Priority Data
Nov. 13, 2013 (DE) .......................... 10 2013 018 917

(51) Int. Cl.
*G01V 3/02* (2006.01)
*G01V 3/04* (2006.01)
(Continued)

(52) U.S. Cl.
CPC ........... *G01N 27/048* (2013.01); *G01N 33/20* (2013.01); *G01N 33/24* (2013.01); *G01N 33/383* (2013.01);
(Continued)

(58) Field of Classification Search
CPC ... G01V 3/02; G01V 3/04; G01V 3/06; G01V 3/08; G01V 3/20; G01V 3/22; G01V 3/24; G01V 3/26; G01N 33/0031
(Continued)

(56) References Cited

U.S. PATENT DOCUMENTS 2,668,202 A    2/1954 Kaplan
6,828,808 B2   12/2004 Srinivasan
(Continued)

FOREIGN PATENT DOCUMENTS

DE    3716846 A1    11/1988
DE    29722546 U1    6/1998
(Continued)

OTHER PUBLICATIONS

JPH06257097 machine translation, Sep. 13, 1994.*
(Continued)

*Primary Examiner* — Huy Q Phan
*Assistant Examiner* — Raul Rios Russo
(74) *Attorney, Agent, or Firm* — Andrew Wilford

(57) ABSTRACT

The invention relates to a system for monitoring a substratum (1) with regard to damage and/or for protecting a substratum (1) from damage. The system comprises: an electrolytically active layer (4), which has a moisture-dependent electrical resistance; at least one electrode pair, the spaced-apart electrodes (3a, 3b) of which are connected to each other by means of the electrolytically active layer (4); and a measuring device, by means of which a property, in particular an electrical quantity of the electrolytically (Continued)

active layer (4) or of the electrodes (3a, 3b), can be measured by using electrodes (3a, 3b) of at least one electrode pair, in particular of each electrode pair, and/or a control device, by means of which a voltage can be applied to the electrodes (3a, 3b) of at least one electrode pair, in particular of each electrode pair. At least one of the electrodes (3a, 3b) of the at least one electrode pair is designed as a planar electrode in the electrolytically active layer (4), in particular the plane of said at least one electrode is oriented parallel to the surface of the substratum (1). The invention further relates to a method for producing a system for monitoring and/or for protecting a substratum, to a method for monitoring a substratum with regard to damage, and to a method for protecting a substratum from damage, in particular moisture damage and/or damage as a result of the penetration of harmful substances.

16 Claims, 1 Drawing Sheet

(51) Int. Cl.
    *G01N 27/04*     (2006.01)
    *G01V 3/06*     (2006.01)
    *G01V 3/08*     (2006.01)
    *G01N 33/38*     (2006.01)
    *G01N 33/20*     (2006.01)
    *G01N 33/24*     (2006.01)
    *G01V 3/20*     (2006.01)
    *G01V 3/22*     (2006.01)

(52) U.S. Cl.
    CPC .............. *G01V 3/02* (2013.01); *G01V 3/04* (2013.01); *G01V 3/06* (2013.01); *G01V 3/08* (2013.01); *G01V 3/20* (2013.01); *G01V 3/22* (2013.01)

(58) Field of Classification Search
    USPC .......... 324/64, 323, 347, 354, 357, 376, 437
    See application file for complete search history.

(56) References Cited

U.S. PATENT DOCUMENTS

| | | | |
|---|---|---|---|
| 2003/0011387 A1* | 1/2003 | Trejo | G01N 17/006 324/700 |
| 2004/0188246 A1* | 9/2004 | Tran | B82Y 30/00 204/267 |
| 2007/0068814 A1* | 3/2007 | Marshall | B01D 61/56 204/553 |
| 2007/0187854 A1* | 8/2007 | Sirola | C04B 28/04 264/35 |
| 2011/0162960 A1* | 7/2011 | Yang | C25D 11/02 204/196.01 |
| 2014/0144779 A1* | 5/2014 | Jeong | B03C 5/02 204/536 |

FOREIGN PATENT DOCUMENTS

| | | |
|---|---|---|
| DE | 202004004766 U1 | 7/2004 |
| DE | 12008032629 A1 | 1/2010 |
| DE | 102011056548 A1 | 6/2013 |
| JP | H06257097 B | 9/1984 |
| WO | 1984001626 A | 4/1984 |

OTHER PUBLICATIONS

DE 102008032629 machine translation, Jan. 14, 2010.*
Martinez, I et al; Corrosion Characterization of Reinforced . . . ; vol. 1 No. 2 p. 107-123; Feb. 1, 2008;XP001511551.

* cited by examiner

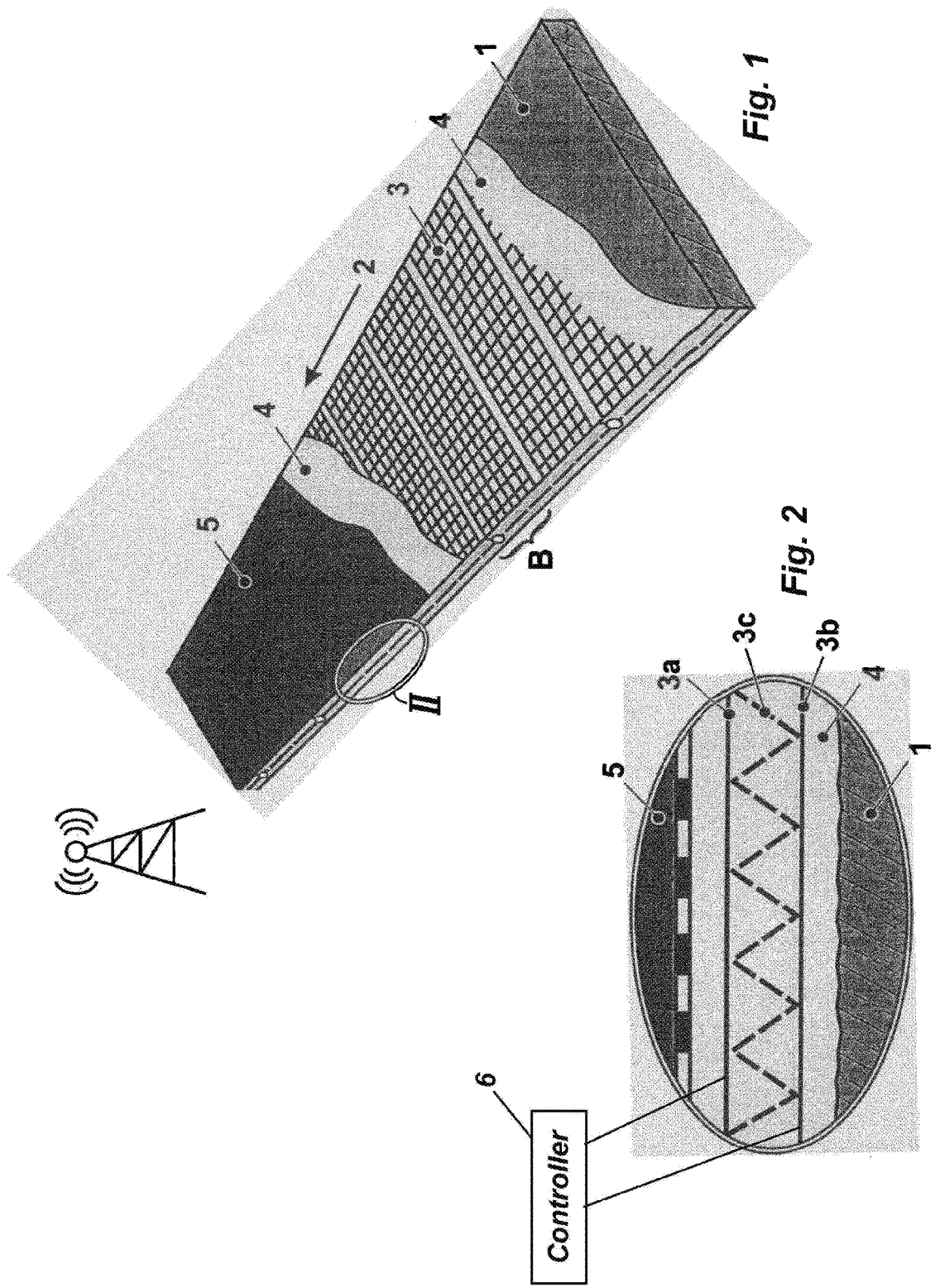

METHOD AND APPARATUS FOR MONITORING AN UNDERGROUND OBJECT

CROSS REFERENCE TO RELATED APPLICATIONS

This application is the US-national stage of PCT application PCT/EP2014/003040 filed 13 Nov. 2014 and claiming the priority of German patent application 102013018917.9 itself filed 13 Nov. 2013.

FIELD OF THE INVENTION

The invention relates to a system for monitoring an underground object with regard to damage and/or for protecting an underground object from damage. The invention further relates to a method of monitoring or also protecting an underground object with regard to damage, as well as a method of making such a system.

BACKGROUND OF THE INVENTION

In the prior art it is known that underground objects, for example underground structures such as those made of steel-reinforced concrete, can suffer damage, for example if they are exposed to moisture in particular from chemical elements introduced into the underground object with the moisture. Thus for example damage can occur when the moisture penetrates into the underground structure and a steel reinforcement present therein begins to corrode as a result, in particular when salts with chloride ions, are introduced into these underground structures by the moisture. This can occur for example from exposure to deicing salt in winter, in particular in the case of roadways that qualify as underground structures.

In the context of the invention, underground objects may be, in addition to the roadways referred to here as an example, in particular bridge structures forming a roadway, as well as other, in particular statically loaded structures, particularly those made of concrete and in particular those made of steel-reinforced concrete or also of other cement-bound materials, in particular hydraulically setting materials.

However, the invention is not limited to underground structures made of steel-reinforced concrete. Also underground structures made purely of metal, for example steel girders or also pure soil, for example below disposal sites, can and should be monitored by a system according to the invention and, if applicable, also protected against damage, for example moisture damage or damage from to chemical contamination.

Previous systems for monitoring and/or for protecting underground objects with regard to damage, such as for example moisture damage, provide for sealing of such an underground object to be carried out, in particular above an underground object, in order to prevent moisture and substances potentially transported therewith from penetrating into these underground objects. Such sealing is sometimes not carried out with the appropriate care or can age in the course of time, leaking as a result, and thus over time allow damage to an underground object.

In the context of the invention damage is regarded not only as damage caused by moisture, but also the ingress of moisture itself, for example from damage in a seal.

Previous systems for monitoring underground objects with regard to damage, such as for example moisture damage, provide for example for mobile devices that travel over the surface of an underground object, for example the concrete surface of an underground structure made of steel-reinforced concrete engaging electrodes with the underground structure and measuring voltage potentials, in order thus to enable corrosion in the steel reinforcement of an underground structure to be traced. Such systems are complex and labor-intensive and can only conduct monitoring on demand, but do not offer a permanent monitoring facility. Furthermore, such systems cannot be used on coated underground objects.

Such systems also have the disadvantage that only damage that has already occurred can be identified, but an incident that will lead to consequential damage, such as for example the appearance of moisture, for example in the event of a damaged seal, cannot be detected before the occurrence of further damage.

OBJECT OF THE INVENTION

Therefore it is an object of the invention to provide a system for monitoring an underground object with regard to damage, in particular with regard to moisture damage, and/or for protecting an underground structure from damage, particularly moisture damage, which system can be used in particular without the intervention of personnel, more preferably permanently and furthermore preferably over a large surface area in any underground objects and preferably in underground structures, such as for example those of roadways, bridges or other structures. It is a further object to provide such a system that is preferably part of an overall construction in conjunction with the underground object, or the underground structure, and thus is permanently connected to the underground object/structure and is put to use together therewith.

Furthermore, an object is to provide, in conjunction with such a system, a method of continuously monitoring over a large area and/or for protecting an underground object, and also to provide a manufacturing method that can be carried out economically and reliably.

SUMMARY OF THE INVENTION

This object is achieved according to the invention by a system of the above-described type in which this system comprises an electrolytically active layer having a moisture-dependent electrical resistance, and at least one electrode pair whose spaced electrodes are connected to each other by the electrolytically active layer in particular are electrically connected to each other, and the system further comprises a measuring device, by means of which a property, in particular an electrical property of the electrolytically active layer or of the electrodes can be measured with the aid of electrodes of at least one electrode pair, in particular of each electrode pair, and/or a controller by means of which a voltage can be applied to the electrodes of at least one electrode pair, at least one of the electrodes of the at least one electrode pair being designed as a planar electrode in the electrolytically active layer, the plane of the at least one electrode being in particular oriented parallel to a surface of the underground object.

An electrolytically active layer is understood here to be a layer that either originally already forms an electrolyte, i.e. even without an incident causing damage, but also at least after an incident causing damage, such as for example moisture ingress into the layer. Thus the layer must at least be designed so that ion migration in the layer is possible, for example after it has become moist. Thus at least when an incident causing damage occurs, such as moisture ingress, the layer becomes electrically conductive if it is not also already electrically conductive before the incident.

Accordingly, a system of the type according to the invention always comprises at least one electrode pair consisting of two electrodes electrically connected to each other by the electrically conductive and electrolytically active layer, so that these two electrodes of the at least one electrode pair can detect a property of this layer, preferably an electrical variable of the layer, by a measuring device and with reference to the measured variable, in particular of the specific value of this variable a conclusion can be drawn as to whether an incident causing damage has taken place.

In principle the invention can provide that any type of property, in particular an electrical property of the layer, can be monitored by measuring a measurable electrical variable, and from a change of the measured value or dropping out of the measured value from a tolerance range or in the event that a comparative value used for a comparison is overwritten or is not reached, a conclusion is drawn that a damage incident occurred and this is signaled. A monitoring measurement can take place repeatedly over time, so that also a development over time can be observed and evaluated.

An embodiment can for example provide that the electrical resistance of the electrolytically active layer is monitored as a property.

Accordingly, in the context of a method of monitoring an underground object provision may be made to measure the resistance between the electrodes and to compare it with a predetermined resistance comparison value, and if the measured value is below the comparison value from increasing moisture in the layer between the at least two electrodes, this falling below the value can be signaled as an incident.

Signaling can generally be carried out for example by long-distance signals, such as a wireless transmission, so that maintenance personnel, for example in a remote control center, can be informed that an incident causing damage, for example an ingress of moisture, has occurred in such a region that is monitored by the surface size of the planar electrode.

For example, after completion of an underground object or an underground structure and installation of a system according to the invention therein, that a measured value can be detected for the monitored property, for example the resistance between the electrodes, which represents a damage-free reference state, in particular a dry reference state, and thus can be used in future as a comparison value for measurements in order to indicate or to signal a future occurrence of damage, for example ingress of moisture between the electrodes, on the basis of a value that is below or above a comparison value, for example the comparison resistance measurement value.

Instead of or in addition to the monitoring of the resistance value, in other embodiments provision may also be made for example for the electrical impedance or a voltage applied between the two electrodes or a current that flows through the electrodes and the electrolytically active layer or the nonconductivity of the electrolytically active layer or the chemical composition of the electrolytically active layer, in particular of the electrolyte of this layer or the pH value of the electrolytically active layer or the temperature the electrolytically active layer to be monitored and measured, in particular no longer to signal tolerable deviations. Variables can also be monitored that are not directly measured but that result from a plurality of other measurements. In particular, a property of the electrodes themselves can be measured, for example by the electrode polarization. For this purpose, electrode materials can be selected that have a sensitivity, in particular sufficiently high sensitivity, to the required property to be monitored.

Suitable underground objects in which the system or also a method of monitoring can be used are in nonlimiting listing for example soil, a disposal site, a concrete substructure, in particular a steel-reinforced substructure, preferably a road or bridge, or generally underground objects consisting of cement-bound materials, in particular with metal reinforcement.

In a nonlimiting exemplary listing the electrolytically active layer may for example be formed by a cementitious hardened layer, in particular a hydraulically, latent-hydraulically or pozzolanically hardened layer, such as for example mortar or concrete, or by an open-pored electrolyte-free structure, in particular an open-pored electrolyte-free foam that can take in an electrolyte in its open pores in the event of a damage incident, in particular becoming conductive in this way, or by an open-pored electrolyte-filled structure, in particular an open-pored electrolyte-filled foam, in particular by changing the electrolyte composition if a damage incident occurs, or for example also by a gel, in particular of which the moisture, for example of water can be changed. Systems according to the invention with these layers or also other layers not mentioned here or for the underground objects mentioned here or also not mentioned here can be combined with all further embodiments referred to in this description.

A method of protecting an underground object from moisture damage can also provide that a controller applies a voltage between at least two electrodes of a system of the type described above. This can take place for example for the purpose of generating a diffusion barrier.

Thus by the application of a voltage between two electrodes an electrical field is generated with a field direction indicated by the positive or negative sign of the voltage difference between the electrodes, which field can serve as a barrier for ions, for example chloride ions, so that by such a method, in particular after detection of a moisture incident, at least the penetration of damaging components, such as for example chloride ions or also other ions, can be prevented effectively by a diffusion barrier formed in this way.

Cathodic protection against corrosion can also be achieved by the application of a voltage.

Such a method of protecting an underground object or an underground structure can be used independently of the previously specified method of monitoring an underground object or an underground structure, but in a special embodiment that is complementary thereto, namely in particular when an incident causing damage, for example an ingress of moisture into the system according to the invention, has previously been detected in the context of the monitoring.

For this, instead of a measuring device previously provided for the purpose of verification, in particular a resistance measurement, after detection of a damage incident, in particular by ingress of moisture between the monitored electrode pair or into the electrolytically active layer, can disconnect the measuring device from the electrodes and instead the controller is connected to the electrodes in order to apply a voltage to the electrodes, in particular in order then to establish the diffusion barrier and/or a cathodic protection against corrosion.

Accordingly, in particular a time for upcoming maintenance after a damage incident can be ignored better without the possibility of significant damage occurring in the meantime in the underground object or in the underground structure, since a protection against corrosion is achieved in the meantime.

An embodiment of the system according to the invention can provide here that such a system is fastened or secured in accordance with the method directly to an underground object or an underground structure, in particular a steel-reinforced concrete underground structure.

For this purpose, for example, it is possible to use the electrolytically active layer or the material that also forms this layer in which at least one electrode of the at least one pair of electrodes present in the system is arranged. Adhesive layer materials, such as for example the cement-bound materials referred to in the introduction, in particular mortar or concrete or foaming glues are ideal for this.

Accordingly, such a material or the layer produced therefrom can assume not only the function of an electrolytically active environment around this at least one electrode, but also a fastening function in order to achieve a nonpositively and/or positively engaged connection to the underground object or an underground structure.

However, in this case fastening does not absolutely have to take place. The possibility also exists of applying a system according to the invention only to an underground object or to achieve bonding only by adhesion. Thus if need be a later residue-free removal of such a system can also take place.

In this case according to an embodiment of the system a first electrode of a pair of electrodes is formed by the planar electrode in the electrolytically active layer, for example the concrete layer and a second electrode of a pair of electrodes is formed by the underground object itself (if this is conductive) or an electrically conductive element located therein, such as for example by a metal reinforcement of the underground structure, in particular if the underground object is formed by steel-reinforced concrete.

This embodiment of the system has the advantage that one of the two electrodes of the at least one pair of electrodes present is already formed directly by elements of the underground object or of the substructure, specifically for example by reinforcing elements, in particular reinforcing bars or reinforcing mesh. Thus accordingly a measuring device referred to in the introduction or a controller can be connected both to the metal reinforcement of the substructure and also to a planar electrode arranged in the concrete layer and thus can perform the functions described in the introduction. Accordingly, such a system for monitoring or for protection of an underground object or an underground structure can be produced particularly cost-effectively, since it merely requires the installation of a further electrode or a plurality of planar electrodes adjacent one another above the reinforcing elements.

In such a design of the system it may be disadvantageous that detected moisture in the region between a planar electrode and the underground object or the reinforcing elements has already penetrated into the underground object/structure and thus already when the ingress of moisture is signaled damage can also immediately occur in the underground structure. Thus in general first the occurrence of damage to the underground object or the underground structure is detected.

According to a preferred modification of the system according to the invention a first electrode of a pair of electrodes is formed by the planar electrode in the electrolytically active layer, for example the concrete layer and a second electrode of a pair of electrodes is formed by a further, in particular likewise planar electrode in the same electrolytically active layer, in particular concrete layer, and particularly preferably both electrodes in the concrete layer are formed with the same area and the same shape and are aligned with each other in a spacing direction and more preferably are parallel but spaced.

Thus with such a version of the system the entire system can be implemented autonomously, without the substrate or elements of the underground structure to be protected or monitored also being incorporated into the system.

Furthermore this version of the system has the advantage that the under-/overshooting of at least one comparison value in the measurement of a property, such as for example the resistance between two electrodes of such a pair of electrodes formed in the layer in such a way indicates that there is damage above the underground object, but not yet in the underground object or the underground structure, that is to say for example moisture has penetrated between the two electrodes of the monitored pair of electrodes, but not yet into the underground object or the underground structure itself, since according to the invention the system for monitoring or for protecting an underground object/structure is above the underground object or the underground structure to be monitored or to be protected.

Accordingly, for example in the first metrological assessment, moisture has indeed infiltrated into a region between the electrodes, but not yet into the underground structure itself.

In particular in this case it is advisable if the method of monitoring an underground object/structure is combined with the method already described beforehand for protecting an underground object/structure in order then after detection of an incident causing damage, such as for example an ingress of moisture in the system, to protect the underground object/structure lying below it by applying a voltage to the monitored electrodes of the electrode pair or also to other electrodes within the system according to the invention, in order to form the diffusion barrier against ions already described in the introduction and/or a cathodic protection against corrosion and thus to prevent damage to the underground object or elements in the underground structure.

Although here in the context of the description of the system the invention is preferably described predominantly in a realization with two electrodes and thus a pair of electrodes within the electrolytically active layer, for example the concrete layer of the system, according to a version of the invention the system has more than two electrodes of the previously described type within the layer, for example the concrete layer, so that in the vertical direction above an underground object or an underground structure local profiles of the monitored property, for example moisture profiles, can be captured, for example by measurement of the electrical resistances between pairs of electrodes at different levels in the layer, in particular the concrete layer already described.

In particular, when more than two electrodes are used, particularly the previously described planar electrodes, the underground object or the underground structure itself can also be incorporated into the system, as here too elements of the substrate, for example the reinforcement, are used as a further electrode for forming a pair of electrodes with such an electrode inside the electrolytically active layer, preferably the concrete/

It is also possible, for example, for a voltage to be permanently generated between the reinforcement and an electrode lying above it in the layer in order to produce a diffusion barrier or a cathodic protection against corrosion, and a specific property, for example the resistance, is measured between a pair of electrodes located thereabove.

The planar electrodes described in the introduction, of which at least one is provided within an electrolytically active layer, for example a concrete layer, above the underground structure to be protected or to be monitored, but preferably at least two electrodes are arranged inside the layer, for example the concrete layer, may for example be formed as a layer of electrically conductive fibers that are incorporated in a matrix material, for example in mortar or concrete.

Fibers that can be used here are particularly preferably carbon fibers, since these are themselves conductive, but do not themselves corrode and thus they offer special advantages in connection with the invention. For example, such a layer of electrically conductive fibers can be formed by mixing the matrix material, such as for example mortar or concrete, with the electrically conductive fibers and applying such a mixture in a planar manner either directly on the underground object/structure or initially on a matrix material layer applied thereto without fibers, for example a concrete layer without fibers, so that ultimately after production of the system according to the invention at least one such layer, preferably two such layers, are arranged within the above-described electrically conductive and electrolytically active layer with moisture-variable electrical resistance. Thus preferably without a fiber component the above-described matrix material, which as a mixture with fibers can form a planar electrode, can also form the material of the electrolytically active layer.

It should preferably be ensured that the matrix material mixture with fibers has a higher electrical conductivity and thus a lower electrical resistance than the material, in particular the same matrix material of the electrolytically active layer in which this electrically conductive layer is embedded.

In an embodiment that is preferable to this, a planar electrode can be formed by a planar conductive electrode element with holes in the surface of the electrode element.

For example, such an electrode element can be formed by a metal or also by a nonmetal, but at least conductive, perforated electrode element, and the perforation does not have to have a circular cross-section but if required could also have an polygonal shape. For example, a perforated plate or a wire mesh can serve this purpose.

In a further embodiment that is preferable to this, such an electrode element can be formed as a textile mat or mesh made of electrically conductive fibers, in particular a fabric made of conductive fibers, in particular in which the mesh openings formed in the mesh correspond to the above-described holes.

When holes are present, for example mesh openings, it is regarded as advantageous if the holes or the mesh openings have a cross-section that is greater than the largest solid components in the layer material of the electrolytically active layer, that is to say for example greater than the maximum particle size of the mortar or concrete forming this layer in which such an electrode element or a pair consisting of two such electrode elements is contained. As a result, these solid components can readily extend through the holes and thus the electrode elements can act in the layer, for example in the mortar/concrete without loosening the layer.

When a pair of electrodes is formed from such materials, in particular from textile meshes or mat products, provision may be made accordingly for the respective mesh/mat product, which forms one electrode of such a pair, to be introduced into the layer (for example the concrete) and spaced apart from the other electrode by the layer material (the concrete). Thus at least two planar electrodes made of the mesh/mat product and lying one above the other in the vertical direction are arranged within the electrolytically active layer, in order between these electrodes to measure the required property, for example the resistance, or for protection to apply a voltage.

When a pair of electrodes is used within the electrolytically active layer, an embodiment is regarded as particularly advantageous in which the pair of electrodes consisting of two layers of a mat product or mesh made of conductive fibers is already kept spaced apart as a unit, in particular a prefabricated unit. For this purpose, the two layers of the mat products/meshes are kept spaced apart by a woven fabric of nonconductive fibers, in particular of synthetic fibers. In this case the woven fabric can preferably in each case also surround the fibers of the mat product/mesh, so that the two meshes/mat products and the woven fabric form a structural unit, in particular one that can also can be rolled up.

In this embodiment the pair of electrodes can very easily be held ready as a prefabricated structural part, in order to place it on an underground object or an underground structure, either directly onto the underground structure or into a connecting layer initially applied thereto, in particular a mortar layer or concrete layer.

The electrodes can then be embedded in the connecting layer, for example the mortar or concrete layer, by further application of layer material, for example mortar or concrete that is distributed through the mesh openings/holes and thus through the electrodes so that ultimately a system according to the invention is produced, and a pair of electrodes made of meshes/mat products spaced apart by the spacer web is embedded in the electrolytically conductive layer, in particular the mortar or concrete layer.

In another alternative, as a planar electrode a nonconductive support element can be coated so as to electrically conductive.

Accordingly a method that is preferably used according to the invention of making a system for monitoring and/or for protecting an underground object/an underground structure can generally provide that at least one planar, in particular prefabricated electrode element or at least one pair consisting of two planar, in particular prefabricated and spaced-apart electrode elements that form a structural unit, in particular where each electrode element comprises a mesh or mat product made of conductive fibers, are laid out on an underground object or an underground structure, such as for example a roadway, and such laying out can take place for example by unrolling from a reel.

Since such electrode elements, in particular prefabricated, or pairs of electrodes can only be produced with a defined maximum area, the invention may further provide that the laying out of at least one such planar, in particular prefabricated electrode element or in particular prefabricated pair consisting of two electrode elements multiple times in at least one direction repeatedly adjacent to each other, takes place in particular in the direction of extension of the underground object of the underground structure, in order thus to be able to monitor or protect a large surface of the underground object/structure, and a monitored or protectable surface area is defined by each in particular prefabricated electrode element or pair of two electrode elements.

For example, when used in road/bridge building, electrode elements or prefabricated pairs consisting of two electrode elements, in particular those that are already connected to each other and spaced apart by spacer elements, are provided at a manufacturing length that corresponds to the width of a roadway or also the width of two or also more roadways, in particular also the width of one or more two-way roadways. Then transversely to the roadway direction the electrode elements can in each case overlap the entire road width or at least complete roadway parts thereof, and can be laid adjacent to each other multiple times in the road extension direction.

By embedding of such an electrode element, in particular prefabricated, or pair consisting of two electrode elements, in particular already prefabricated and connected with spacer web, at the same time a fastening to an underground object/an underground structure can take place, specifically with the same layer material, in particular mortar or concrete that can also be used for embedding the at least one planar electrode in the electrolytically active layer.

Each electrode or each pair of electrodes can be connected according to the invention to a respective measuring device for measuring a property, in particular an electrical property, and preferably the electrical resistance between two electrodes and/or to a control system for applying a voltage between two electrodes, in order to achieve the monitoring and/or the protection of the surface area that is covered by the area of an electrode element or in particular a prefabricated pair of electrode elements or in particular a prefabricated pair.

BRIEF DESCRIPTION OF THE DRAWING

An embodiment of the invention is described in greater detail below with reference to a drawing, in which:

FIG. 1 shows the system in connection with a bridge 1 or generally with a roadway 1 as an underground structure to be protected; and FIG. 2 shows in larger scale the detail indicated at II in FIG. 1.

SPECIFIC DESCRIPTION OF THE INVENTION

In this embodiment, in the direction of the longitudinal extent or travel direction 2 prefabricated pairs of spaced electrodes 3 extend transversely across the roadway, and according to the detail view each pair of electrodes 3 comprises an upper mesh 3a and a lower mesh 3b that are spaced apart by a spacer web 3c.

In this embodiment the spacer web is formed of nonconductive plastic fibers, and the two meshes 3a and 3b are formed from conductive fibers, for example carbon fibers, and the mesh has a mesh size that is greater than the maximum particle size of the concrete forming the concrete layer 4 in which the prefabricated pair of electrodes 3 is embedded. The meshes and the spacer web form a structural unit here.

Alternatively, of course, wire meshes can also be used as electrode elements, in particular those that are already kept at a fixed spacing by nonconductive spacers and form a prefabricated structural part.

According to the invention, a concrete layer is applied to an underground structure, such as in this case the roadway 1, a prefabricated electrode element 3 with at least one pair of electrodes is introduced into this concrete layer, in particular transversely with respect to the roadway direction, the electrode element 3 and the internal cavities thereof are filled with the concrete and covered with concrete, so that overall a concrete layer 4 is produced in which the prefabricated pair of electrodes is embedded.

Here the concrete for the concrete layer 4 is selected such that the electrical resistance thereof is dependent upon the moisture of the concrete. Thus the concrete forms an electrolytically active layer in the sense of the invention.

Thus by a resistance measurement between the meshes 3a and 3b, which serve here as electrode surfaces with an open surface, it is possible to detect whether moisture has penetrated into the concrete layer 4.

The underground structure 1 is immediately adjacent the bottom of the concrete layer 4, and a further roadway structure 5 of basically any type can lie atop the concrete layer 4 and thus above the system according to the invention. This shows that the system according to the invention can form part of an overall structure such as for example a road, a bridge or some other structure.

The two electrode surfaces formed by the meshes 3a and 3b are connected to a measuring device for the purpose of monitoring the surface area of the underground structure covered by the electrodes 3 for moisture or to form a diffusion barrier for protection by connecting a voltage.

FIG. 1 also shows that because of limited manufacturing widths B of the electrodes 3, a respective electrode element 3 can extend transversely over the entire roadway width and also longitudinally of the roadway, that is to say in the direction of travel, and a plurality of such electrode elements can be arranged one behind the other, so that a large surface area of a roadway as a whole and in principle any length can be monitored.

Each individual electrode 3, which here consists of the meshes 3a and 3b connected to the spacer web 3c, forms a surface that can be monitored and that can be connected to a respective measuring device. Provision may also be made here to connect a plurality of electrodes 3 to the same measuring device that carries out a resistance measurement individually for each electrode.

Provision may also be made here to connect the lower or the upper electrodes to each other, since nevertheless a surface resolution is produced by the associated and individually interconnected opposite electrodes.

When the resistance value is below a resistance boundary value in a pair of electrodes 3, this dropping below the value is signaled visually, acoustically or by telecommunication. Accordingly, the measuring device can comprise a transmitter that sends a warning message about the detected ingress of moisture to a controller 6 or other monitoring center for example via mobile wireless. This same controller can also apply a voltage differential across the electrodes 3a and 3b.

Just as the possibility is provided here of connecting the electrodes formed by the meshes 3a and 3b to a measuring device in order to measure the resistance between these electrodes, provision may likewise be provided for applying a voltage to these electrodes for protection and in particular for formation of a diffusion barrier and/or cathodic protection against corrosion between the electrode surfaces or meshes 3a and 3b.

Depending upon the direction of the electrical field formed hereby, a diffusion barrier for either positively or negatively charged ions is formed, so that for example a field direction or voltage polarity can be selected in order to form a diffusion barrier for chloride ions, since this type of ion most likely occurs from ingress of deicing salt on a roadway surface.

Due to the flexibility of the electrodes 3 because of the formation as a mesh connected to spacer web, a manufacturing method may provide here that such prefabricated electrode elements are unrolled into a concrete bed transversely with respect to the roadway direction or are unrolled directly onto the dry underground structure 1 and then can be embedded in the layer 4 by application of concrete. Thus the system according to the invention is formed in the underground structure and can then be equipped with further structures, for example a roadway surface.

Thus the system according to the invention then forms for the future an element that is inseparably connected to the overall structure that can be used continuously for monitoring or for protecting the underground structure.

The invention claimed is:

1. A system for monitoring an underground object with regard to damage and/or for protecting an underground object from damage, the system comprising:
   an electrolytically active and cementitious hardened layer having a moisture-dependent electrical resistance and partially comprised of aggregate particles having a predetermined maximum particle size;
   a pair of spaced-apart electrodes electrical connection with each other through the electrolytically active cementitious layer;
   a measuring device for measuring an electrical property of the electrolytically active layer or of the electrodes with the aid of the electrodes of the a electrode pair; and
   a controller for applying a voltage to the electrodes of the electrode pair, one of the electrodes of the electrode pair being formed by a mesh made of conductive fibers as a planar electrode in the electrolytically active layer, the mesh having mesh openings of a size greater than the particles of the cementitious layer such that the cementitious layer extends through the mesh.

2. The system according to claim 1, wherein both of the electrodes are formed as meshes made of conductive fibers and are repeatedly laid adjacent to each other multiple times repeatedly in a direction of extension of the underground object.

3. The system according to claim 1, wherein the electrical variable is one of the following:
   electrical resistance;
   electrical impedance;
   a voltage that is applied between the two electrodes;
   a current that flows through the electrodes and the electrolytically active layer;
   the dielectricity of the electrolytically active layer.

4. The system according to claim 3, wherein the property is determined from an electrical variable according to claim 3, and in particular the property is one of the following:
   the chemical composition of the electrolytically active layer, in particular of the electrolyte of this layer;
   the pH value of the electrolytically active layer; or
   the temperature of the electrolytically active layer.

5. The system according to claim 1, wherein the underground object is formed by a of the following:
   soil;
   a disposal site;
   a concrete substructure, in particular a steel-reinforced substructure, preferably a road or bridge; or
   a metal structure.

6. The system according to claim 1, wherein the cementitious hardened layer is a hydraulically, latent-hydraulically or pozzolanically hardened layer, preferably mortar or concrete.

7. The system according claim 1, wherein the system is fastened to the underground object by the cementitious hardened layer.

8. The system according to claim 1, wherein a first electrode of the pair of electrodes is formed by the mesh in the electrolytically active layer and a second electrode of the pair of electrodes is formed by the underground object itself or an electrically conductive element located therein.

9. The system according to claim 1, wherein a first electrode of the pair of electrodes is formed by the mesh in the electrolytically active layer and a second electrode of the pair of electrodes is formed by a further also planar electrode in the electrolytically active layer, the two electrodes in the electrolytically active layer having the same area and aligned one behind the other in a spacing direction.

10. The system according to claim 1, wherein the pair of electrodes is formed as two planar meshes made of conductive fibers, the two meshes being spaced apart by a woven fabric of nonconductive fibers.

11. The system according to claim 1, wherein each pair of electrode elements forms a region that can be individually monitored and/or protected.

12. A method of making a system for monitoring and/or for protecting an underground object, wherein one of the planar electrode elements or at least a pair of two planar and spaced-apart electrode elements are each formed by a mesh made of conductive fibers on an underground object and are surrounded with an electrically conductive layer whose conductivity depends upon the moisture of the layer, so that a layer forms in which at least one of the planar electrode elements is embedded and the electrodes are connected to a measuring device for measuring a property between two electrodes and/or to a controller for applying a voltage between two electrodes.

13. The method according to claim 12, wherein the mesh made of conductive fibers is unrolled on the underground object.

14. The method according to claim 12, wherein the laying out or unrolling takes place multiple times repeatedly adjacent each other in a direction of extension of the underground object.

15. A method of monitoring an underground object with regard to moisture damage, the method comprising the steps of:
   measuring an electrical variable for the electrical resistance between the electrodes of the system between at least two electrodes of a system according to claim 1;
   measuring the value for the electrical resistance between the electrodes;
   comparing the measured value with a comparison value, and
   issuing a signal if the measured value is below or above the a one comparison value from increasing moisture between the at least two electrodes.

16. A method of protecting an underground object from moisture damage and/or damage from the penetration of pollutants, comprising the steps of:
   applying with a controller between at least two electrodes of a system according to claim 12 a voltage difference in order to produce a diffusion barrier or a cathodic corrosion protection, the application of the voltage taking place automatically after signaling the undershooting or overshooting of the a comparison value between the electrodes.

* * * * *